United States Patent [19]

Sarumaru et al.

[11] Patent Number: 5,077,434

[45] Date of Patent: Dec. 31, 1991

[54] PROCESS FOR PRODUCTION OF ACRYLIC ACID

[75] Inventors: Kohei Sarumaru, Ami; Takeshi Shibano, Yokkaichi, both of Japan

[73] Assignee: Mitsubishi Petrochemical Company Limited, Tokyo, Japan

[21] Appl. No.: 129,749

[22] Filed: Dec. 7, 1987

[30] Foreign Application Priority Data

Dec. 11, 1986 [JP] Japan ................. 61-295216

[51] Int. Cl.⁵ ............................................. C07C 51/25
[52] U.S. Cl. .................................... 562/534; 562/535; 568/479
[58] Field of Search ................. 562/534, 535; 568/479

[56] References Cited

U.S. PATENT DOCUMENTS

| | | | |
|---|---|---|---|
| 4,031,135 | 6/1977 | Engelbach et al. | 562/535 |
| 4,365,087 | 12/1982 | Kadowaki et al. | 562/534 |
| 4,837,360 | 6/1989 | Kadowaki et al. | 562/546 |

FOREIGN PATENT DOCUMENTS 108208  8/1975  Japan ................. 562/513

*Primary Examiner*—Jose G. Dees
*Attorney, Agent, or Firm*—Oblon, Spivak, McClelland, Maier & Neustadt

[57] ABSTRACT

Vapor phase catalytic oxidation of propylene into acrolein in the first step and then into acrylic acid in the second step has been improved (1) by utilizing as a diluent for the oxidation in the first step the effluent gas from the second step after the acrylic acid produced has been recovered therefrom and after it has been catalytically combusted and (2) by specifying operation conditions set in view of the recycle of the combusted "waste" gas.

The improved process, embodying the present invention, has made it possible to produce a high concentration of acrylic acid as both gas and condensation and also to prolong the catalytic activity of a Mo-Bi composite oxide catalyst used for the first oxidation reaction.

10 Claims, 1 Drawing Sheet

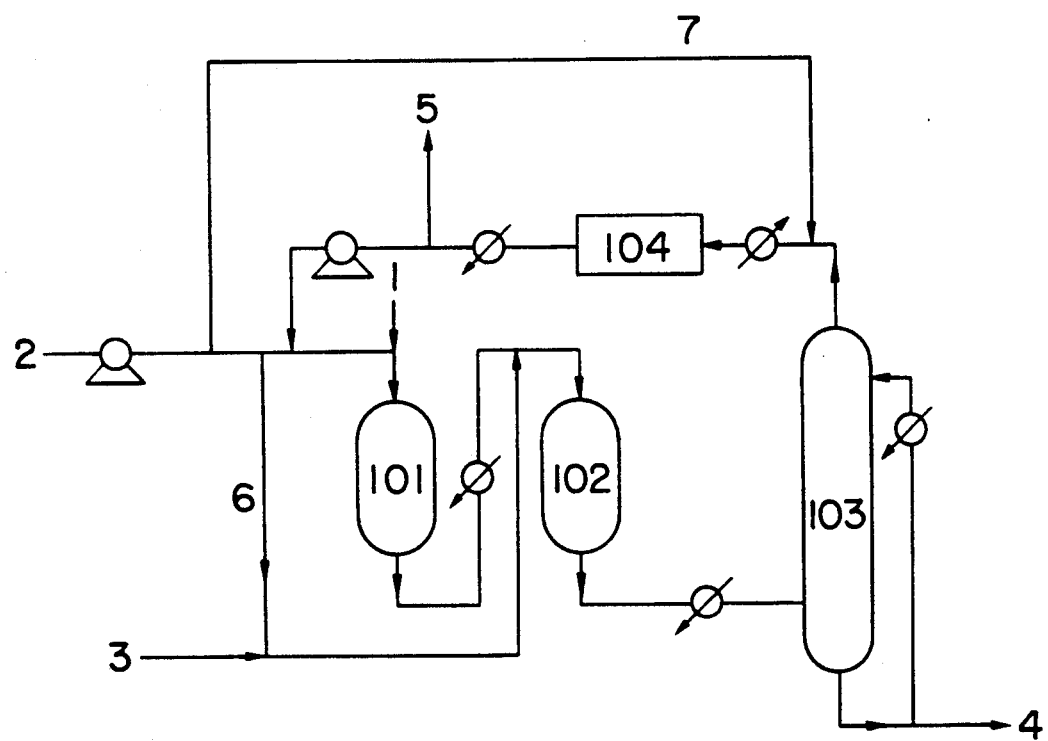

PROCESS FOR PRODUCTION OF ACRYLIC ACID

BACKGROUND OF THE INVENTION

1. Field of the Invention

The present invention relates to a process for producing acrylic acid by vapor phase catalytic oxidation of propylene in two steps. More particularly, the invention relates to a process for producing an aqueous solution of acrylic acid of a high concentration by oxidation of propylene at a high concentration and also providing with prolonged catalytic activity a Mo-Bi composite oxide catalyst used for vapor phase catalytic oxidation in the first step.

2. Discussion of the Background

The process for producing acrylic acid by vapor phase catalytic oxidation in two steps using molecular oxygen is already known and used on an industrial scale.

One of the typical processes for industrial production is as follows. Propylene is converted mainly into acrolein and a small amount of acrylic acid in the first step by supplying a mixture of propylene, air and steam, and the product is supplied to the second reactor without separation of products. In this case, the method of adding a new air and steam required for the subsequent reaction in the second step, at the inlet of the second reactor is also known and described, for example, in Japanese Patent Laid-Open Publication No. 73041/1981.

Another typical process is that wherein the product gas containing acrylic acid obtained at the outlet of the second reactor is introduced into a collecting apparatus to obtain acrylic acid as an aqueous solution and a part of remaining waste gas containing unreacted propylene coming out from the collecting apparatus is reused by adding it at the first reactor inlet together with the starting gas mixture of propylene, air and steam. A part of unreacted propylene is recycled in this method, which is described in, for example, Japanese Patent Publication No. 30688/1978 and Japanese Patent Laid-Open Publication Nos. 108917/1977, 15314/1978 and 36415/1976.

These two typical processes are classified into two major categories, the former being a process without recycling (hereinafter referred to as the non-recycling process or one-pass process) and the latter being one recycling the waste gas containing unreacted propylene (hereinafter referred to as the unreacted propylene recycling process).

A lot of improved methods of the non-recycling and unreacted propylene recycling processes have been proposed respectively in the references cited above to produce in a large scale acrylic acid efficiently by vapor phase catalytic oxidation of propylene. Among all these proposals, the most important issue is how to increase the space time yield of acrylic acid as gas and the acrylic acid concentration in the condensate obtained.

On the other hand, it is apparent that the economy of these processes is greatly influenced by the performance of the oxidation catalysts used, and many proposals with respect to catalysts have been presented, for example, in Japanese Patent Publication Nos. 17711/1972, 27490/1972, 41329/1972, 42241/1972, 42813/1972, 1645/1973, 4763/1973, 4764/1973, and 4765/1973 for the first step catalysts, and Japanese Patent Publication Nos. 12129/1969, 19296/1973, 169/1974, 11371/1974, 10432/1977, 31326/1977 and Japanese Patent Laid-Open Publication Nos. 2011/1971, 8360/1972 and 43922/1974 for the second step catalysts.

The currently used catalysts for industrial production are mainly Mo-Bi composite oxide catalysts for the first step and Mo-V composite oxide catalysts for the second step.

There are many reasons why the characteristics of these oxidation catalysts greatly affect the economy of the processes. Primarily the selectivity of the catalysts for the reactions affects the quantity of propylene used, and the catalyst activity in the reactions affects the space time yield of acrylic acid. Furthermore, the catalyst life and its price affect the total catalyst cost. Further, the applicability of the catalysts to various reaction conditions affects the quantity of energies used for the reactions.

SUMMARY OF THE INVENTION

Study which has led to the present invention

All of the catalysts now used industrially in practice should be outstanding in their catalyst properties. They all would seem to be applicable to both non-recycling and unreacted propylene recycling processes. The inventors have found the existence of a superior industrial process for acrylic acid production disclosed hereinafter through investigating intensively the natures of Mo-Bi composite oxide catalysts used in the first step and Mo-V composite oxide catalysts used in the second step.

The following is a summary of the basic results elucidated by our investigation in the process of arriving at our invention.

(1) Steam is not essential in the first step, but is essential in the second step when Mo-Bi composite oxide catalysts [(Mo-Bi) catalysts] and Mo-V composite oxide catalysts [(Mo-V) catalysts] are used in the first and second steps, respectively.

(2) The catalyst activity of (Mo-Bi) catalysts for the first step is seriously impaired by the addition of acrylic acid, acetic acid and the like to the starting gas mixture. Accordingly, the unreacted propylene recycling process requires a complicated control in the maintenance of the composition of the recycled waste gas.

(3) In the recycle process, the higher the concentration of the propylene in the first reactor inlet is, the smaller must be the waste gas ratio in the mixed gas supplied at the first reactor inlet governed by the quantity of air supplied to the first reactor inlet. Accordingly, the recovery of unreacted propylene in the recycle process is not much if a condition of a high concentration of propylene in the first step reaction is to be used.

(4) One of the crucial factors affecting the catalyst life of (Mo-Bi) catalysts is the partial pressure of steam at the first reactor inlet. Lowering of this pressure as much as possible is advantageous.

As a result of our analysis of these findings, we have discovered that a process which comprises: introducing the acrylic acid-containing product gas obtained at the second reactor outlet into an acrylic acid-collecting apparatus; collecting acrylic acid as an aqueous solution; subjecting all the waste gas from the collecting apparatus to catalytic combustion oxidation thereby converting the unreacted propylene in the waste gas mainly into $CO_2$ and $H_2O$; and adding a part of the combusted waste gas thus obtained to the gas mixture supplied to the first reactor inlet (this process being referred to hereinafter as the combusted waste gas recycling process) is an industrial process for producing acrylic acid which is superior to the unreacted propylene recycling process known heretofore.

It is disclosed in Japanese Patent Publication No. 30688/1978 that the gas remaining after removal of the most part of the condensable gas, obtained at the second reactor outlet is introduced again at the first reactor inlet as a substitution of a part or all of the steam supplied as inert dilution gas. This reference, however, does not refer to any of the conditions in which the inert dilution gas is reused. The present invention is characterized by subjecting the entire quantity of the above waste gas with additional air supplied to combustion in an ordinary combustion apparatus for waste gas with an oxidation catalyst, e.g. a noble metal catalyst and introducing again a part of the resulting combusted gas to the first reactor inlet. At this time, the concentrations of air and waste gas at the first reactor inlet are established according to the oxygen concentration of combusted waste gas. Further, a large portion of oxygen and steam required for the reaction in the second step can be freshly supplied at the second reactor inlet in certain cases.

Summary of the Invention

As described above, to establish a safe and economical industrial process for producing acrylic acid by catalytic oxidation of propylene, we have investigated the fundamentals relating to the oxidation process including elucidation of properties of oxidation catalysts, precise measurement of explosion limits and the like, and found several important facts.

The present invention has been achieved on the basis of these new findings and provides a process for producing acrylic acid in a high space-time-yield as a condensate of a high concentration by oxidation of propylene at a high concentration under specific restricted conditions and also for prolonging catalytic activity.

The present invention is characterized by the conditions for oxidation reactions in acrylic acid production process by two step vapor phase catalytic oxidation, which comprises converting propylene mainly into acrolein by subjecting a gas mixture containing propylene, molecular oxygen and an inert gas to the first catalytic oxidation and then subjecting the product gas from the first reaction to the second catalytic oxidation reaction optionally together with steam added, and the oxidation conditions used in accordance with the present invention are as follows.

A. The catalyst for the first catalytic oxidation reaction is a Mo-Bi based composite oxide catalyst and that for the second catalytic oxidation reaction is a Mo-V based composite oxide catalyst.

B. The product gas resulting from the second catalytic oxidation reaction is subjected to an acrylic acid recovery step where the acrylic acid is recovered as an aqueous solution, and all of the remaining waste gas obtained from the acrylic acid recovery step is subjected to catalytic oxidation combustion; and a part of combusted waste gas is recycled to the first reactor.

C. The composition of the reaction gas subjected to the first catalytic oxidation reaction is as follows.

The molar ratio of molecular oxygen to propylene is 1.17 to 2.50; the concentration of the propylene is 5 to 14%; and the concentration of the combusted waste gas is 5 to 95%.

In one embodiment of the present invention, the gas to be subjected to the second catalytic oxidation reaction resulting from the first oxidation reaction and an optional gas mixture added comprising molecular oxygen and steam has the following composition, the composition being indicated as the sum of the gas to be fed to the first oxidation reaction and the optional gas mixture added: the molar ratio of the molecular oxygen to the propylene being 1.75 to 2.50, and the molar ratio of the steam to the propylene being 0.5 to 5.0.

According to the present invention, it is possible without complicated control to utilize waste gas from the second reactor outlet as dilution gas at the first reactor inlet and to obtain acrylic acid of a high concentration in a high space time yield and a condensate of high acrylic acid concentration and to prevent the first step catalyst from deterioration. Further disposal of the waste gas can be carried out simultaneously.

BRIEF DESCRIPTION OF THE DRAWING

In the drawing, the single FIGURE is a flow chart indicating an example of the process of the present invention.

DESCRIPTION OF THE PREFERRED EMBODIMENT

Analysis of the Reactions Involved

The results of our investigation of the fundamentals, by which the present invention has been achieved, are described below.

The inventors used (Mo-Bi) catalysts comprising Mo-Bi-Fe-Co-Ni-B-Na-K-Si-O as the first step catalyst and (Mo-V) catalysts comprising Mo-V-Sb-Ni-Nb-Cu-Si-O as the second step catalyst. The following results were obtained.

By investigation of the effect of various compounds added to starting substances it was found that addition of acrylic acid and acetic acid resulted in a decrease of conversion of propylene, but other carbonyl compounds of a low boiling point had very little effect on the conversion of propylene. This result not only supported the disclosure in Japanese Patent Laid-Open Publication No. 108917/1977 which had indicated the necessity of strict control of recycled waste gas so as not to contain these acids in the proplyene recycling process but also emphasized that complete elimination of acids is highly preferable. Further, it was found that coexistence of steam was not required for the starting material composition in the first reaction if the starting material was diluted with inert gas. In addition, it was shown that low oxygen and steam pressure resulted in severe decrease of conversion of acrolein, and also steam was requisite for the second reaction by investigation of the composition of the gas supplied at the second reactor inlet.

On the contrary, we presumed that the major factor in the deterioration of (Mo-Bi) catalysts is deficiency of Mo on the catalyst's surface, as indicated in U.S. Pat. No. 4,604,370, which probably results from sublimation of Mo.

The relation between steam pressure at the first reactor inlet and decrement of Mo on the catalyst's surface has been investigated by using ESCA. It has been found that the amount of sublimated Mo increases with increment of steam pressure. The result is in principle similar to those described in the references such as Journal of Physical Chemistry 69, No. 6, 2065-2071 (1965) and Angewandte Chemie 75, No. 20, 947–957 (1963). The results of the references, however, were obtained by the use of molybdenum trioxide and by the use of much higher temperatures than those for industrial use. Differently from those experiments, our investigation, on the contrary, has been carried out under such conditions as are used for an industrial operation, with industrial catalysts. The sublimation rate of Mo has been found to be much lower than that obtained by extrapolation from the data in the references cited above.

In addition, from the viewpoint of environmental pollution, discharged waste gas must be completely combusted before it is discharged in an industrial plant for acrylic acid production.

There are two methods for combustion of waste gas: one is by burning oil, and the other is catalytic oxidation combustion by the use of a catalyst, such as a noble metal catalyst. Recently the technology for catalytic oxidation combustion has been highly improved to cause waste gas to burn very stably. The concentration of oxygen in waste gas combusted completely can be measured continuously and very stably. As contrasted with the completely combusted gas, waste gas such as in a recycling process which contains much organic compounds and presents difficulty in continuous analysis of oxygen concentration and requires zero point compensation continually for accurate analysis, and it can be concluded that the combusted waste gas recycling process is superior to the unreacted propylene recycling process.

Based on the findings described above, we have improved the system disclosed in Japanese Patent Laid-Open Publication No. 73041/1981 and now achieved the present invention which relates to a simplified and safe combusted waste gas recycling process.

The present invention can be used more advantageously when such propylene of a lower purity is used as, for example, propylene fraction with high content of propane obtainable from an FCC plant or with high content of $H_2$ obtainable from dehydrogenation of propane.

Specific Practice of Reaction

The present invention is characterized by a combination of procedural steps, and catalysts and unit operations and unit reactions themselves can be those known in the art or modified ones.

Although the catalysts are important elements in catalytic oxidation reaction to which the present invention belongs, (Mo-Bi) catalysts for the first reaction and (Mo-V) catalysts for the second reaction may be those disclosed in the above-mentioned Japanese Patent Laid Open Publications and Japanese patent Publications. Suitable catalysts are, for instance, those represented by the following formulas. These formulas, however, are those used commonly to indicate the name and the contents of elements in the catalyst and do not mean chemical compounds which have the molecular formula.

(1) Mo-Bi Based Composite Oxide Catalyst:

$Mo_{12}Bi_aFe_bCo_cNi_d(B, P$ and/or $As)_e (M$ and/or $Tl)_fM'_gW_hSi_iO_x$ wherein M stands for an alkali metal and M' stands for an alkaline earth metal, and a is 0.5 to 7, b is 0.05 to 3, c is 0 to 10, d is 0 to 10, (c +d) is 1 to 10, e is 0 to 3, f is 0.05 to 1.4, g is 0 to 1.0, h is 0 to 3.0, i is 0 to 48, and x is a number satisfying the oxidation state of the elements included.

(2) Mo-V Based Composite Oxide Catalyst:

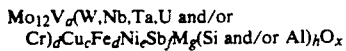

$Mo_{12}V_a(W,Nb,Ta,U$ and/or $Cr)_bCu_cFe_dNi_eSb_fM_g(Si$ and/or $Al)_hO_x$ wherein M stands for an alkali metal, and a is 0.1 to 4, b is 0.1 to 4, c is 0.1 to 4, d is 0 to 2, e is 0 to 24, f is 0 to 50, g is 0 to 2, h is 0 to 100, and x is a number satisfying the oxidation state of the elements included.

Oxidation combustion of waste gas after removing acrylic acid or a tail gas can be carried out by using suitable oxidation catalysts, for instance, noble metal catalysts. Various review articles can be used as detailed reference for oxidation catalysts, such as KOGYO SHOKUBAI HANNO II (INDUSTRIAL CATALYTIC REACTIONS II), pp 206 to 219 published by Kodansha, Japan. These references are herein cited as reference. Particularly suitable oxidation catalysts in the present invention are those comprising Ru, Rh, Pd, Os, Ir or Pt. Pt catalysts are typical.

A particular example of the process of the present invention is indicated in the attached flow chart.

In the embodiment shown in the flow chart, propylene and air are fed to a first step reactor 101 where the propylene is converted mainly to acrolein, and the effluent gas from the first step reactor 101 is sent to a second step reactor 102 where the acrolein is converted mainly to acrylic acid. The effluent gas from the second step reactor 103 is sent to a quenching column 103 where the effluent gas is quenched to form an aqueous solution of the acrylic acid leaving a waste gas or a tail gas, and the aqueous acrylic acid thus formed is withdrawn via line 4. The waste gas is withdrawn from the quenching column 103 through out of its top, and is then sent to a combustion furnace 104 where the waste gas undergoes catalytic oxidation combustion. A part of the effluent gas from the furnace 104 is sent to the first step reactor 101 in accordance with the present invention. The remaining of the combusted waste gas is withdrawn from the system via line 5. Steam is fed to the second step reactor via line 3. Air may be supplied to the second step reactor and/or the furnace 104 upon necessity via lines 6 and 7, respectively. Blowers or pumps and heat exchangers are provided on the lines where required.

In the illustrated process, air and steam supplied at the second reactor inlet can be replaced by air suitably moistened in advance. Further, this process has an advantage in that the oxygen concentration in combusted waste gas can be controlled irrespectively of the preceding reactions by the amount of secondary air supplied at the inlet of the combustion apparatus.

Example

A catalyst of the following atomic ratio was produced in the manner used commonly as the composite oxide catalyst for the first reaction.

Mo:12, Bi:5, Ni:3, Co:2, Fe:0.4, Na:0.2, B:0.4, K:0.1, Si:24, 0:x in which x is determined by the oxidized state of individual metal elements concerned.

A catalyst of the following atomic ratio was also produced in the manner used commonly as the composite oxide catalyst for the second reaction.

Sb:100, Ni:43, Mo:35, V:7, Nb:3, Cu:9, Si:20, 0:x, in which x is determined by the oxidized condition of individual metal elements concerned.

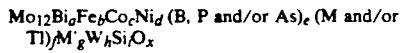

The reactor has a double pipe construction made of stainless steel. The inner pipe is 20 m/m in inner diameter and 2,200 m/m in length, while the outer pipe is 100 m/m in inner diameter and 1,900 m/m in length. The catalyst is filled in the inner pipe and a molten nitrate bath is filled between the inner and the outer pipes so that a uniform temperature of the catalyst in the inner pipe can be maintained by stirring the nitrate bath.

Two sets of the reactor of above type were joined together with a connection pipe and were used as the first and the second reactors, respectively.

First, the first reactor was charged with 200 ml of ceramic balls to form a bed for preheating on the inlet side of the reactor. Subsequently 250 ml of the first reactor catalyst diluted with 250 ml of ceramic balls was placed in the first reactor to form a catalyst bed, and the first reactor was further charged on the outlet side with ceramic balls. The second reactor was treated similarly as the first reactor except that 167 ml of the second reactor catalyst diluted with 167 ml of ceramic balls was used to form a second reaction catalyst bed.

In the meantime, waste gas from the acrylic acid production plant was combusted using a Pt-catalyst, "Cataform NM-12" supplied by Nikki Universal Co., Ltd., Japan. The results of composition analyses of the waste gas and the combusted waste gas were as follows.

| Waste gas | Combusted waste gas |
|---|---|
| $O_2$:6.0% | $O_2$:4.3% |
| CO:0.9% | CO:less than 0.1% |
| $CO_2$:2.5% | $CO_2$:4.6% |
| $H_2O$:4.0% | $H_2O$:5.3% |
| $N_2$:86% | $N_2$:85.7% |
| $C_3$:0.5% | propane:trace |
| acrolein:0.01% | propylene:trace |
| acetic acid:0.03% | |

Based on the above result, the starting gas composition supplied at the first reactor inlet was set at the level as follows.
propylene:10%
combusted waste gas:25%
air:65%

The starting gas actually supplied at the first inlet was composed of 10% of propylene, 70.1% of air, 17.4% of $N_2$, 1.2% of $CO_2$ and 1.3% of steam. This composition was in good agreement with the level set.

To the second reactor inlet, additional air and steam were supplied to make up the following molar ratios to which the gas composition supplied at the first inlet was taken into account.
molecular oxygen/propylene:2.1
steam/propylene:2.0

The average yield of acrylic acid was 88.4% under the following conditions:
nitrate bath temperature in the first reactor: 340° C.
nitrate bath temperature in the second reactor: 260° C.
pressure at the first reactor inlet: 0.8 kg/cm²G
pressure at the second reactor inlet: 0.6 kg/cm²G The space-time-yield obtained was 164 g acrylic acid/lit.catalyst.hr.

What is claimed is:

1. In a two-step process for production of acrylic acid which comprises subjecting a gas mixture comprising propylene, molecular oxygen and an inert gas to a first step catalytic oxidation reaction thereby to convert the propylene mainly into acrolein and subjecting the gas mixture obtained from the first step oxidation reaction optionally added with a gas mixture comprising molecular oxygen and steam to a second step oxidation reaction thereby to convert the acrolein mainly into acrylic acid, the improvement which comprises conducting the oxidation reactions under the following conditions:

A: a Mo-Bi based composite oxide catalyst is used for the first step catalytic oxidation reaction and a Mo-V based composite oxide catalyst is used for the second step catalytic oxidation reaction;

B: the product gas resulting from the second step oxidation reaction in subjected to an acrylic acid recovery step where the acrylic acid is recovered as an aqueous solution, a total quantity of the waste gas obtained from the acrylic acid recovery step is subjected to catalytic oxidation combustion, and a part of the combusted waste gas is recycled to the first step catalytic oxidation reaction; and C: the gas mixture to be subjected to the first step catalytic oxidation reaction is in the state of:
a molar ratio of the molecular molecular oxygen to the propylene of from 1.17 to 2.50;
a concentration of the propylene of from 5 to 14%; and
a concentration of the combusted waste gas of from 5 to 95%.

2. A process as claimed in claim 1 in which, in the supplying of the gas produced in the first step catalytic oxidation reaction to the second step catalytic oxidation reaction, the gas to be supplied to this second step catalyst oxidation reaction is, as a result of the addition of the gas mixture comprising molecular oxygen and steam, depending on the case, in the state of:
a molar ratio of the molecular oxygen to the propylene of from 1.75 to 2.50; and
a molar ratio of the steam to the propylene of 0.5 to 5.0,
in which each ratio is represented as the sum of the quantities of said gas mixture and the gas mixture for the first contact oxidation reaction.

3. The process of claim 1, comprising using, as said Mo-Bi based composite oxide catalyst, a Mo-Bi-Fe-Co-Ni-B-Na-K-Si-O catalyst.

4. The process of claim 1, comprising using, as the Mo-V catalyst, a Mo-V-Sb-Ni-Nb-Cu-Si-O catalyst.

5. The process of claim 1, comprising using as a propylene-containing gas mixture a propylene-containing gas mixture containing a high content of propane.

6. The process of claim 1, comprising using as a propylene-containing gas mixture a propylene-containing gas mixture having a high content of hydrogen and obtained from the dehydrogenation of propane.

7. The process of claim 1, comprising using as said Mo-Bi based composite oxide catalyst a Mo-Bi based composite oxide catalyst of the formula:

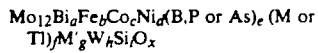

wherein M stands for an alkali metal and M' stands for an alkaline earth metal, and a is 0.5 to 7, b is 0.05 to 3, c is 0 to 10, d is 0 to 10, (C+d) is 1 to 10, e is 0 to 3, f is 0.05 to 1.4, g is 0 to 1.0, h is 0 to 3.0, i is 0 to 48, and x is a number satisfying the oxidation state of the elements included.

8. The process of claim 1, comprising using as said Mo-V based composite oxide catalyst a Mo-V based composite oxide catalyst of the formula:

$$Mo_{12}V_a(W, Nb, Ta, U \text{ or } Cr)_bCu_cFe_dNi_eSb_fM_g(Si \text{ or } Al)_hO_x$$

wherein M stands for an alkali metal, and a is 0.1 to 4, b is 0.1 to 4, c is 0.1 to 4, d is 0 to 2, e is 0 to 24, f is 0 to 50, g is 0 to 2, h is 0 to 100, and x is a number satisfying the oxidation state of the elements included.

9. The process of claim 1, comprising subjecting said waste gas to catalytic oxidation combustion over an oxidation catalyst comprising Ru, Rh, Pd, Os, Ir or Pt.

10. The process of claim 1, comprising subjecting said waste gas to catalytic oxidation combustion over a Pt oxidation catalyst.

* * * * *